United States Patent [19]

Leveque et al.

[11] Patent Number: 5,944,667
[45] Date of Patent: Aug. 31, 1999

[54] DEVICE FOR EVALUATING THE CREASING OF THE SKIN IN VIVO

[75] Inventors: Jean-Luc Leveque, Le Raincy; Pierre Corcuff, Neuilly-sur-Marne; Jean Mignot, Thise, all of France

[73] Assignee: L'Oreal, Paris, France

[21] Appl. No.: 08/930,577

[22] PCT Filed: Feb. 13, 1997

[86] PCT No.: PCT/FR97/00278

§ 371 Date: Jan. 16, 1998

§ 102(e) Date: Jan. 16, 1998

[87] PCT Pub. No.: WO97/29686

PCT Pub. Date: Aug. 21, 1997

[30] Foreign Application Priority Data

Feb. 16, 1996 [FR] France .................................. 96 01968

[51] Int. Cl.⁶ .................................................. A61B 5/00
[52] U.S. Cl. .......................................... 600/473; 600/476
[58] Field of Search .................................. 600/407, 473, 600/475–478

[56] References Cited

U.S. PATENT DOCUMENTS 5,054,502 10/1991 Courage ................................... 600/476
5,146,923 9/1992 Dhawan ................................... 600/476

FOREIGN PATENT DOCUMENTS 0 373 332 A1 6/1990 European Pat. Off. .
2 607 929 6/1988 France .

OTHER PUBLICATIONS

Zahouani et al "Theoretical and experimental study of wound healing: application to leg ulcers" Medical & Biological Engineering & Computing pp. 234–238, Mar. 1992.
Assoul et al "Three–dimensional measurements of skin topography by triangulation with a new laser profilometer" Journal of Medical Engineering & Technology vol. 18 No. 1 pp. 11–21, Jan. 1994.

Primary Examiner—Ruth S. Smith
Attorney, Agent, or Firm—Oblon, Spivak, McClelland, Maier & Neustadt, P.C.

[57] ABSTRACT

A device for evaluating the creasing of the skin in vivo. A zone of the skin to be examined is creased. The zone of the creased skin is scanned with an incident luminous beam which is emitted by a light source. The light reflected by the creased skin is detected. The detected light is converted into an electrical signal. At least one parameter representing the profile of the creased skin is extracted from the electrical signal. This device makes it possible to evaluate the mechanical properties of the dermis, such as its elasticity and firmness and the aging of the skin, as well as to evaluate the effectiveness of products intended to counteract such aging.

20 Claims, 1 Drawing Sheet

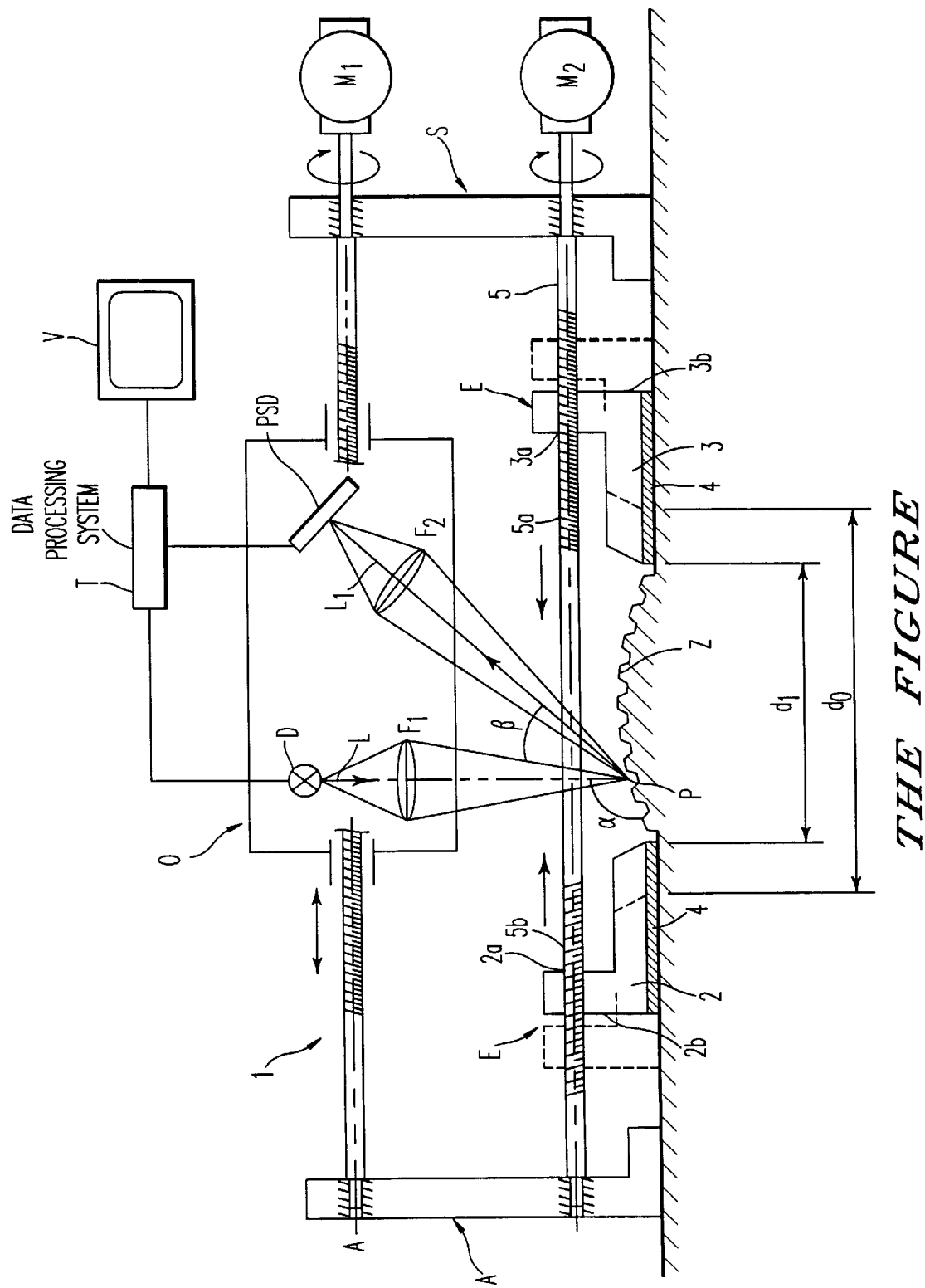
THE FIGURE

DEVICE FOR EVALUATING THE CREASING OF THE SKIN IN VIVO

BACKGROUND OF THE INVENTION

1. Field of the Invention

The present invention relates to a device and a method for evaluating the deformation of the surface of the skin, in particular of the skin in vivo. More particularly, the invention relates to a device for the profilometry of the human skin, aiming at evaluating the mechanical properties of the dermis, such as its elasticity and its firmness, or the state of the ageing of the skin, by measuring in a simple and fast manner the depth of the creases induced by deformation. This device is, moreover, suitable for evaluating in series the effectiveness of new basic materials and formulations for counteracting the ageing of the skin which are developed in cosmetic or dermo-pharmaceutical laboratories. Thanks to this new device tests of the ageing of the skin can also be performed at the dermatologist or institutes for cosmetic care, without any need for relying on long and complicated procedures.

2. Discussion of the Background

From the Article of M. Assoul et al. "Three dimensional measurement of skin surface topography by triangulation with new laser profilometer" which appeared in the J. of Med. Eng. and Tech., 1994, 18, 11–21, a device is known for evaluating the state of the surface of the skin in vitro, using resin replicas reproduced on the basis of a skin specimen. These replicas are examined by means of an optoelectronic device operating according to the triangulation method. The prior art device for thus evaluating the state of the skin surface on the basis of resin replicas allows accurate results to be obtained but it is not suitable, on the one hand, for an evaluation in series, in particular in vivo, requiring the preparation and evaluation of the replicas by a specialist and, on the other hand, for permitting an evaluation in a short time.

FR-A-2 607 929 describes a system for a one-way mechanical deformation of the human skin, but does not mention the optical processing of the results of this deformation in any way. Moreover, this document is not explicit as regards the type of deformation applied to the skin. Furthermore, this system does not make it possible to adapt an optoelectronic device of the above mentioned kind in a simple manner.

SUMMARY OF THE INVENTION

The object of the present invention is to improve this known device and to adapt it to the evaluation, in series, of deformations of the skin produced in a number of individuals; the cost of such a device is to be advantageous. The aim of the invention is, in particular, the fast evaluation of the relief of the surface of the skin after a deformation induced in vivo; it can be used by unqualified staff in cosmetic institutes, medical analytical laboratories or hospitals. In particular, the aim of the invention is to obtain the result of this evaluation in a virtually instantaneous manner.

Thus, the first aspect of the present invention is a device for evaluating in vivo the creasing of the skin, in particular of the human skin, comprising:

a) movable means for creasing a zone of the skin to be examined, parallel to its surface;

b) movable means for scanning the zone of the creased skin with an incident light beam emitted by a light source;

c) means for detecting the light diffusely reflected by the creased skin;

d) means for converting the detected light into an electrical signal; and e) means for extracting from the electrical signal at least one parameter representing the profile of the creased skin.

The means for detecting the reflected light comprise one or advantageously several position detectors.

Advantageously, the detection of the light reflected by the illuminated creased skin is effected either (i) according to the triangulation method (see the article by the above mentioned M. Assoul together with Lee C S, Kim S W, Yim D Y, "An in process measurement technique using the laser for non-contact monitoring of roughness surface and form accuracy of ground surfaces". Annals CIRP 1987: 36: 332–339), or (ii) according to the focusing method.

The triangulation method lies in passing a light beam onto a surface to be examined at a given angle of incidence, for instance 45°. The position of the transmitted light beam is registered by a position detector. It is also possible to pass an incident light beam at an angle of substantially 0°, and to register the reflected light by two position detectors disposed at 45° from the axis of the incident light in a plane which contains the axis of the incident beam. By way of simplification, it is preferable to use a single detector.

According to an alternative, a so-called focusing method is used. With this focusing method a lens for focusing the incident light beam is displaced relative to the surface to be examined, so as to be always focused onto the surface to be investigated, and one registers the light beam reflected by a detector disposed symmetrically to the incident beam relative to the normal of the surface to be investigated.

Advantageously, the parameter of the profile of the skin is chosen from the following parameters: $R_t$, $R_a$, $S_m$, R and AR, etc . . . , $R_t$ being the maximum height of a crease, $R_a$ being the arithmetic mean of all the points of the profile, evaluated relative to the median line of the creases, $S_m$ being the mean value of the horizontal interspacing between the creases evaluated at the level of the median line of the profile, R being the mean depth of the whole set of creases and AR being the mean interspacing between the creases.

Advantageously, the means for creasing the skin comprise two plates situated at a given interspacing $d_o$ from each other, and means for moving these plates towards each other by reducing the interspacing $d_o$, so that the zone of the skin is subject to creasing over a reduced zone $d_1$, the movable means for scanning the zone of the creased skin being displaced parallel to the surface of the skin, in the direction of the crease.

To ensure a good adhesion of the plates on the zone of skin to be examined, the side of these plates in contact with the skin may be covered by an adhesive, to fix them momentarily on either side of said zone of the creased skin. Tests effected by the Applicant have shown that good results can be obtained by sticking these plates to the forearm of the person to be examined, for example, by means of a double-sided adhesive tape.

Advantageously, the creasing of the zone of the skin to be examined is effected in such a way that $d_o-d_1$ represents approximately 2% to 50% of $d_o$. The best results were obtained by the Applicant with a value of $d_0-d_1$ of approximately 5 to 20% of $d_o$, and more particularly of 10%.

Advantageously, the bringing together of the plates can be controlled by a first electric motor connected to a shaft provided, for example, with a first portion comprising a right-hand thread, and a second portion comprising a left-hand thread. These portions of the motor shaft each cooperate with a plate carrier element comprising an internal thread complementary to the thread of the motor shaft. Thus by rotating the motor shaft, it is possible to cause the distance between the two plates to vary automatically, and to obtain the desired creasing of the skin by bringing the plates towards each other.

The plate carriers, as well as the motor, may be mounted on a frame. Advantageously, this frame carries an optoelectronic system, movable in translation along the direction of the creasing of the skin. This translation may be automatically ensured by a second electric motor equipped with an adequate drive mechanism. The optoelectronic system comprises means for detecting the light reflected by the illuminated creased skin, the detection means being formed, for example, by at least one position detector. Moreover, the optoelectronic system comprises the light source constituting the means for illuminating the zone of the creased skin, this light source emitting the incident light beam.

More precisely the light source, as well as the means for detecting the reflected light, are mounted in a fixed position with respect to each other and are movable relative to the zone of the skin to be examined. By this arrangement, the means for detecting the reflected light can simultaneously execute the same translational movement as the light source.

With a view to simplifying the measurements of the parameters and to obtain them with precision, the light source is mounted on the support in such a way that the angle of incidence of the light beam on the skin is approximately 0°, the detector for registering the reflected light being disposed on an axis forming an angle of reflection of approximately 45° relative to the incident light beam.

Preferably, the light source is a source of a laser beam, but any other light source capable of emitting a light beam, monochromatic or non-monochromatic, could be used. More particularly, the source of the laser beam is a laser diode whose incident light beam has a wave length comprised, for example, in the range extending from 400 nm to 1100 nm, and preferably comprised between 630 and 788 nm.

Moreover, to obtain an optimum resolution of the parameters to be measured, this light beam may be focused on the skin by a first (lens-type) focusing system disposed between the light source and the zone of the skin to be examined.

The means for registering the reflected light are constituted by one or several position detectors (position sensing detectors—PSD) advantageously two in number, converting the collected light into an electrical signal. With a view to obtaining a higher measurement accuracy, it is advantageous to use several detectors. This kind of detector is capable of registering the intensity, as well as the position of a reflected light beam incident on its surface.

Advantageously, a second focusing system is disposed between the skin zone and the position detector, which focusing system recovers, then focuses the light reflected by the skin before the detection. The electrical signal provided by the detector and corresponding to the light diffused on the surface of the detector, is substantially transmitted to a data processing system where it is digitized. This processing system is, moreover, programmed to extract at least one of the above mentioned parameters $R_t$, $R_A$, $S_m$, R and AR . . . of the electrical signal. Means such as a screen or a printer may be provided for displaying the extracted parameters.

A second aspect of the invention is constituted by a method for evaluating the induced relief of the deformation of the surface of the skin in vivo, comprising the steps of:

a) obtaining, in a zone of the skin to be examined, a creasing parallel to its surface by movable means;

b) scanning the zone of the creased skin with an incident light beam transmitted by a light source;

c) detecting the light reflected by the creased skin;

d) converting the detected light into electric signals; and e) extracting from the electrical signals at least one of the parameters representing the profile of the creased skin.

By way of example, the parameter is chosen from the following parameters: $R_t$, $R_a$, $S_m$, R and AR . . . , $R_t$ being the maximum height of a crease, $R_a$ being the arithmetic mean of all the points of the profile, evaluated relative to the median line of the creases, $S_m$ being the mean value of the horizontal interspacing between the creases, evaluated at the level of the median line of the profile, R being the mean depth of the whole set of creases, and AR being the mean interspacing between the creases.

This method is executed by means of the device which has been described above.

Thanks to the device and method of the invention, it is possible to undertake in series the evaluation in vivo of the creasing of the surface of the skin of an individual, or the action of a product on it. This device and method have the advantage of not requiring the employment of a specialist, and can provide results virtually instantaneously at moderate cost. Moreover, the same skin zone can be scanned several times for comparative studies, for example, before and after the application of a treatment product.

BRIEF DESCRIPTION OF THE DRAWING

To render the present invention more readily understood, an embodiment in accordance with the invention, represented in the single attached FIGURE which shows a layout diagram of the device of the invention, will now be described by way of a purely illustrative, and in no way restrictive example.

DETAILED DESCRIPTION OF THE PREFERRED EMBODIMENTS

In this FIGURE, Z designates a zone of the skin, for example the forearm, the creasing of which skin is intended to be examined. On the skin is positioned a frame S comprising a shaft 5 disposed parallel to the surface of the skin and movable in rotation. For this purpose, an electric motor $M_2$ is provided to cause the shaft 5 to rotate. The shaft 5 consists of first and second portions 5a and 5b, the first portion 5a being provided with a left-hand thread and the second portion 5b being provided with a right-hand thread. The portions 5a and 5b engage with internal thread portions 2a and 3a respectively, cut in a plate-carrier element 2b, 3b. The plate-carrier elements respectively support a plate 2, 3 of rectangular shape and having a substantially flat face, intended to come into contact with the skin and forming the means (E) for producing the creasing.

Advantageously, the flat side of the plates has an adhesive layer 4, for example, a double-sided adhesive film. Thanks to this arrangement, the zone Z of the skin to be examined can be immobilized relative to the frame S. The initial interspacing $d_o$ between the plates 2, 3 is, for example, 48 mm. By causing the shaft 5 to rotate by means of the motor $M_2$, these plates are brought towards each other until a distance $d_1 < d_o$, for example 41 mm, is obtained. This bringing together then produces a pinching of the skin of approximately 15%, so that a creasing thereof is produced, forming creases P orientated perpendicularly to the shaft 5. Means (D) for scanning the skin, and means (PSD) for detecting the reflected light are mounted on the frame (S). The frame also carries means (E) for producing the creasing, as well as the light source (D).

The frame S has, moreover, an optoelectronic system 0 mounted for translational movement along a shaft A relative to the frame, the shaft A being parallel to the shaft 5. An electric motor $M_1$ is provided for controlling the translational movement. The optoelectronic system comprises, moreover, a light source, here a laser diode D, capable of emitting a laser beam L of a wave length of 630 to 788 nm. This laser beam L incident on the zone of the skin to be examined forms with its surface an angle α of approximately 0°. To obtain a better resolution, a focusing system $F_1$ is provided between the diode D and the skin zone Z to focus the beam L on the zone Z. The incident beam L is absorbed and reflected by the skin. To allow the quantity of light diffused in the form of a beam $L_1$ to be collected, a PSD sensor (position sensing detector) is disposed in an axis passing through this beam and forming an angle β of approximately 45° with the axis of the incident light L. Between the skin zone Z and the detector PSD the beam $L_1$ passes through a second focusing system $F_2$, focusing this beam on the surface of the detector. The detector PSD is fixedly mounted relative to the laser diode D.

Alternatively a fixed source of radiation is used, the scanning of the zone to be examined being obtained by directing the light beam onto a rotating mirror of a polygonal type with several reflecting facets.

To be able to measure the surface profile of the creased skin zone Z to be examined, the optoelectronic system O is displaced along the axis A by the distance $d_1$. During this translational movement, the beam L scans the skin zone Z between the two plates. At the same time, the sensor PSD registers on the one hand the intensity of the beam $L_1$ and on the other hand the position whereat it arrives on the detector. In point of fact, according to the depth of a crease or a wrinkle P, the beam $L_1$ coming from a zone Z situated at the top of a plate is incident on a portion of the detector PSD different from that reached by the rays coming from the bottom of a crease.

The beams incident on the detector PSD are converted into electrical signals which are transmitted to a data processing system T. This processing system T is programmed according to a mathematical calculation, for example, of the type taught by the above mentioned document of M. Assoul et al., to extract one, or several of the characteristic parameters of the profile of the creased skin, such as the parameters $R_t$, $R_a$, $S_m$, R and AR, $R_t$ being the maximum height of a crease, $R_a$ being the arithmetic mean of all the points of the profile evaluated relative to the median line of the creases, $S_m$ being the mean value of the horizontal interspacing between the creases evaluated at the level of the median line of the profile, R being the mean depth of the whole set of creases, and AR being the mean interspacing between the creases. A screen V is provided to display these parameters.

The device of the invention (apart from the processing system T and apart from the screen V) forms a small portable unit, connected to the processor system by a connecting cable. Because of this, its manipulation is easy during the measurements, both for the individual to be examined and for the operator who undertakes the measurements.

We claim:

1. A device for evaluating the creasing of the skin, comprising:
    movable means for creasing a skin zone to be examined, parallel to a surface of said movable means;
    a light source;
    movable means for scanning the zone of the creased skin with an incident light beam emitted by said light source;
    means for detecting the light reflected by the illuminated creased skin;
    means for converting the detected light into an electrical signal; and
    means for extracting from the electrical signal at least one parameter representing a profile of the creased skin.

2. A device according to claim 1, wherein said light source and said means for detecting the light have locations determined according to a triangulation method.

3. A device according to claim 1, wherein said light source and said means for detecting the light have locations determined according to a focusing method.

4. A device according to claim 1, wherein the at least one parameter is one of the following parameters: $R_t$, $R_a$, $S_m$, R and AR, $R_t$ being the maximum height of a crease, $R_a$ being the arithmetic mean of the height of all the points of the profile, evaluated relative to the median line of the creases, $S_m$ being the mean value of the horizontal interspacing between the creases, evaluated at the level of the median line of the profile, R being the mean depth of the whole set of creases, and AR being the mean interspacing between the creases.

5. A device according to claim 1, wherein the light source and the means for detecting are mounted fixed relative to one another and movable by said movable means relative to the skin zone to be examined.

6. A device according to claim 1, wherein the means for creasing the skin zone comprise two plates situated at a specified distance from one another, and means for bringing the plates towards one another by reducing the distance, so that the skin zone has a creasing over a reduced zone.

7. A device according to claim 6, wherein the plates are covered on a side away from said light source with an adhesive, for fixing them momentarily on either side of the creased skin zone to be examined.

8. A device according to claim 6, wherein a distance by which the specified distance is reduced is approximately 2% to 50% of the specified distance.

9. A device according to claim 6, wherein a distance by which the specified distance is reduced is approximately 5% to 20% of said specified distance.

10. A device according to claim 6, wherein a distance by which the specified distance is reduced is approximately 10% of said specified distance.

11. A device according to claim 1, wherein the light source is a source of a laser beam.

12. A device according to claim 1, wherein the light source emits a light beam having a wave length in a range extending from 400 nm to 1100 nm.

13. A device according to claim 12, wherein the light source is a laser diode whose luminous radiation has a wave length between 630 nm and 788 nm.

14. A device according to claim 1, further comprising:
    a frame;
    wherein the means for scanning the zone of the skin and the means for detecting the reflected light are mounted on said frame also carrying the means for producing the creasing.

15. A device according to claim 14, wherein the light source is also mounted on the frame.

16. A device according to claim 14, wherein the frame is portable and connected by a connecting cable to the means for extracting.

17. A device according to claim 1, wherein the means for detecting comprise at least one position detector.

18. A device according to claim 1, wherein the skin is creased along one direction, and the movable means for scanning the creased skin zone is displaced parallel to the surface of the skin in the direction of the creasing.

19. A device according to claim 1, wherein the means for extracting at least one parameter comprise a system for processing the data provided by the means for detecting.

20. A device according to claim 1, further comprising means for displaying the extracted parameter.

* * * * *